United States Patent [19]

Hahn

[11] Patent Number: 4,969,166
[45] Date of Patent: Nov. 6, 1990

[54] COMPUTER TOMOGRAPHY APPARATUS

[75] Inventor: Guenter Hahn, Neunkirchen am Brand, Fed. Rep. of Germany

[73] Assignee: Siemens Aktiengesellschaft, Berlin and Munich, Fed. Rep. of Germany

[21] Appl. No.: 417,206

[22] Filed: Oct. 4, 1989

[30] Foreign Application Priority Data

Oct. 17, 1988 [EP] European Pat. Off. ........ 88117261.3

[51] Int. Cl.$^5$ .......................................... G01N 23/00
[52] U.S. Cl. .......................................... 378/19; 378/4
[58] Field of Search ................................ 378/4, 19

[56] References Cited

U.S. PATENT DOCUMENTS

| | | | |
|---|---|---|---|
| 3,988,730 | 10/1976 | Valker | 340/412 |
| 4,035,647 | 7/1977 | Hounsfield et al. | 378/19 |
| 4,066,900 | 1/1978 | LeMay | 378/19 |
| 4,091,286 | 5/1978 | Logan et al. | 378/4 |
| 4,134,018 | 1/1979 | Weinkauf et al. | 378/19 |
| 4,220,863 | 9/1980 | McBride et al. | 378/19 |
| 4,377,868 | 3/1983 | Mueller | 378/19 |
| 4,413,351 | 11/1983 | Kowalski | 378/19 |
| 4,484,340 | 11/1984 | Yamaguchi et al. | 378/19 |

FOREIGN PATENT DOCUMENTS 0077471 4/1983 European Pat. Off. .
0140663 8/1983 Japan ........................................ 378/4

Primary Examiner—Craig E. Church
Attorney, Agent, or Firm—Hill, Van Santen, Steadman & Simpson

[57] ABSTRACT

A computer tomography apparatus has a radiation detector formed by a row of detector elements, and a data acquisition system having a detector channel for each detector element. A multiplexer samples the signals of the detector elements. To avoid image artifacts due to differing disturbing influences in the transmission and conversion of the measured values for the individual detector channels, the multiplexer has a number of levels, and is controlled so that sampling of the individual detector channels takes place in changing sequences. A bank of analog-to-digital converters follows the multiplexer, and the allocation of the converters in the bank to groups of detector channels is also changed during data acquisition. The output signals of the analog-to-digital converters, which represent individual outputs for each channel, are entered into a memory in proper numerical sequence.

1 Claim, 2 Drawing Sheets

COMPUTER TOMOGRAPHY APPARATUS

BACKGROUND OF THE INVENTION

1. Field of the Invention

The present invention is directed to a computer tomography apparatus, and in particular to a data acquisition system for sampling the signals from the individual detector elements.

2. Description of the Prior Art

Computer tomography devices are known which have a rotating frame, surrounding a measuring opening for the patient, on which an x-ray source and a radiation detector are mounted. The x-ray source emits a fan-shaped x-ray beam, which penetrates a transverse slice of the patient, with the attenuated radiation being incident on the radiation detector. The rotating frame is rotated through 360° so as to transirradiate the patient from different angles. The radiation detector consists of a plurality of individual detector elements. The detector elements are successively sampled by a multiplexer at defined angular positions, for example, at each angular degree. The sampling takes place in a fixed sequence. As a consequence of this fixed sequence of sampling, even small errors caused by the read-out event for the individual detector channels can be visible in the image generated by a computer from the detector signals.

SUMMARY OF THE INVENTION

It is an object of the present invention to provide a computer tomography apparatus wherein even minute errors caused by the respective read-out events for the individual detector channels do not result in an image artifact.

The above object is achieved in accordance with the principles of the present invention in a computer tomography apparatus having a data acquisition system which includes a multiplexer and a control unit for the multiplexer. The control unit for the multiplexer controls the sequence of sampling of the individual detector elements. Instead of a fixed sampling sequence, a pseudo-random sampling sequence is selected. The aforementioned image errors are thereby avoided.

In a further embodiment of the invention, a bank consisting of a plurality of analog-to-digital converters is used, with each converter receiving the output signals from a different group of detector elements. The control unit also controls the allocation of the channels to the analog-todigital converters, so that the allocation of the channels to the converters is also changed in a pseudo-random manner, so that image errors do to respectively different transmission behavior of the various analog-to-digital converters are also avoided.

DESCRIPTION OF THE PREFERRED EMBODIMENTS

Figure 1:
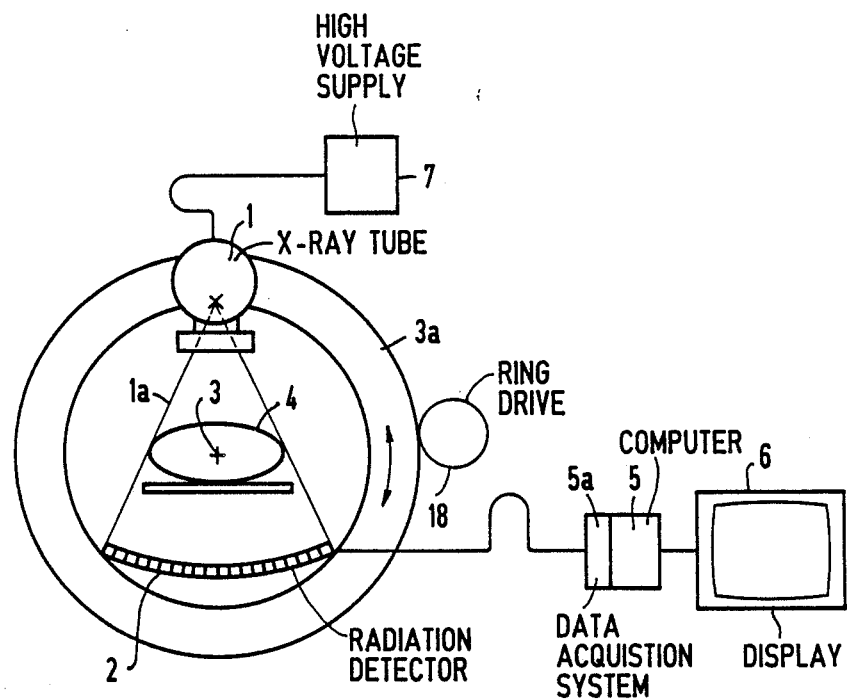
FIG. 1 is a schematic block diagram of a computer tomography apparatus constructed in accordance with the principles of the present invention.

FIG. 1 is a schematic diagram showing the basic components of a computer tomography apparatus of the type in which the invention disclosed herein can be incorporated. The computer tomography apparatus includes an x-ray tube 1, fed by a high voltage supply 7, and a radiation detector 2 which consists of over one hundred, for example 512, individual detector elements, arranged in a row. The x-ray tube 1 emits a fan-shaped radiation beam 1a, having a cross-sectional extent, perpendicular to a slice plane to be examined, which defines the thickness of the slice plane. The x-ray beam 1a is of such a size in the slice plane that the entirety of the patient 4 in the slice plane is penetrated by radiation. The radiation detector 2 is curved around the focus of the x-ray tube 1. The x-ray tube 1 and the radiation detector 2 are mounted on a ring 3a, which is rotatable around an axis 3, in either direction of the double arrow, by a ring drive 18. The axis 3 approximately coincides with the longitudinal axis of the patient 4.

The number of individual detector elements comprising the radiation detector 2 is selected according to the desired image resolution. The output signals from the individual detector elements are supplied to a computer 5, which calculates the attenuation values of a pixel matrix of the transirradiated slice of the patient 4. The matrix is converted into a viewable image and is reproduced on a display 6.

Each detector element of the radiation detector 2 has a measuring channel allocated thereto, which leads to the computer 5. Amplifier circuits, multiplexers and analog-todigital converters, which in combination form a data acquisition system 5a, are provided for each measuring channel. The data acquisition system 5a constructed in accordance with the principles of the present invention is shown in greater detail in FIG. 2.

Figure 2:
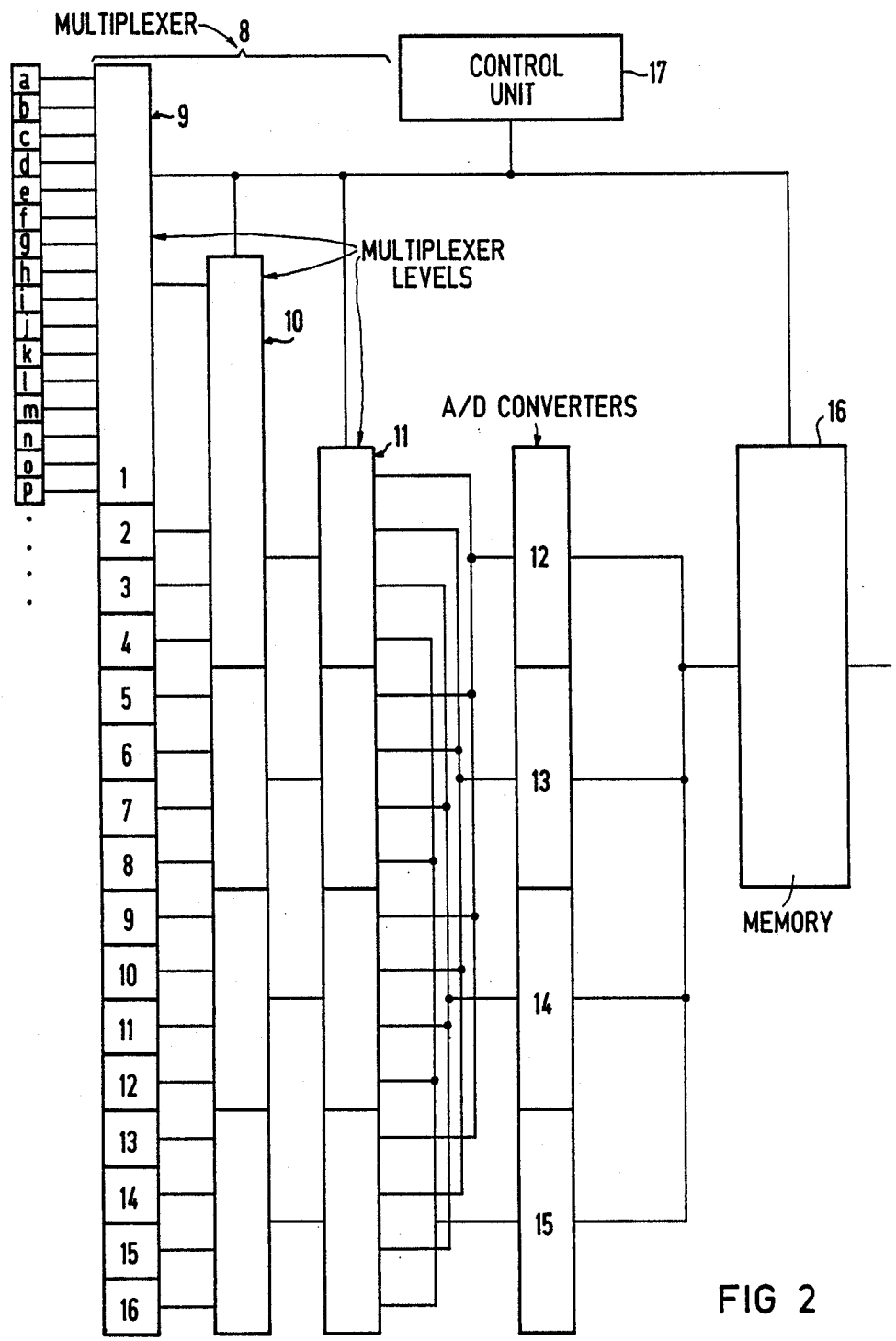
FIG. 2 is a schematic block diagram of the components of a data acquisition system for the computer tomography apparatus of FIG. 1 necessary for explaining the invention.

A series of detector channels a through p are shown in FIG. 2, it being understood that many more such channels, corresponding in number to the number of individual detector elements, are present, but are not shown in FIG. 2. The channels a–p constitute a group. In the embodiment of FIG. 2, the total number of multiplexer channels is divided into sixteen such groups. The signals from the channels a through p are all supplied to a first of these sixteen groups in a first multiplexer level 9 of a multiplexer 8. The multiplexer 8 has a second multiplexer level 10, which combines the groups from the first level 9 into four analog buses. The outputs of the four analog buses are supplied to a third multiplexer level 11, which distributes the analog buses to the respective inputs of four analog-to-digital converters 12, 13, 14 and 15. The outputs of the analog-to-digital converters 12 through 15 are supplied to an input of a memory 16. Addressing of the multiplexer levels 9, 10 and 11 and of the memory 16 is undertaken by a control unit 17.

The control unit 17 is programed so that a change in the sampling sequence of the detector channels is undertaken, by changing the addressing sequence of the multiplexer levels 9 and 10, after each complete read-out event. A change in the bus allocation for the addresses of the multiplexer level 11 ensues after each analog-to-digital conversion cycle.

A plurality of sampling cycles (approximately 400 to 2,000) are required for an image formatting. The above described circuit permits different sampling sequences to be generated pseudo-randomly for the channels a through p, and also permits the allocation of the individual channels to different analog-to-digital converters 12–15 to be undertaken.

The generated digital values are stored in the proper numerical sequence 1, 2, 3...n−1, n in the memory 16. A sorted value set is thus available for further processing by the computer 5 to generate the displayed image.

The important feature of the present invention, as described above, is that the sampling of the signals of the detector elements of the radiation detector 2 occurs in changing sequences for the individual projections during a scan of the slice plane of the examination subject, i.e., during rotation of the ring 3a. If, for example, the ring 3a is rotated through 360° around the patient 4 for producing a tomogram, and one set of detector signals is generated at each degree, then 360 different sequences can be provided for sampling the signals of the detector elements of the radiation detector 2. In accordance with the invention, it is important that the sampling of the signals of the detector elements be changed between the individual projections of a scan event.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus for examining a subject comprising:
    means for generating penetrating radiation in a planar beam, defining a slice, in which said examination subject is disposed;
    a plurality of detector elements disposed to receive radiation in said slice attenuated by said examination subject and generating electrical signals corresponding to the incident, attenuated radiation;
    means for rotating said means for generating penetrating radiation and said detector elements around said patient to conduct a scan;
    a multiplexer having first, second and third multiplexer levels, said first multiplexer level having a set of first multiplexer level inputs and a set of first multiplexer level outputs, said first multiplexer level outputs being fewer than said first multiplexer level inputs so that signals at said first multiplexer level inputs are supplied in different groups to said first multiplexer level outputs, said second multiplexer level having a set of second multiplexer level inputs connected to said set of first multiplexer level outputs and having a set of second multiplexer level outputs, said second multiplexer level outputs being fewer than said second multiplexer level inputs so that signals at said second multiplexer level inputs are supplied in different groups to said second multiplexer level outputs, and said third multiplexer level having a set of third multiplexer level inputs connected to said set of second multiplexer level outputs and having a set of third multiplexer level outputs, said third multiplexer level outputs being fewer than said third multiplexer level inputs so that signals at said third multiplexer level inputs are supplied in different groups to said third multiplexer level outputs;
    a plurality of analog-to-digital converters having respective inputs connected to said set of third multiplexer level outputs, said analog-to-digital converters each having an output;
    a memory having a input connected to said outputs of said analog-to-digital converters; and
    control means for said first, second and third multiplexer levels and said memory for supplying said signals from said detector elements to said inputs of said analog-to-digital converters in a plurality of different sequences during a scan, for changing the connection of said set of third multiplexer level outputs to said analog-to-digital converters during a scan so that signals at said set of third multiplexer level outputs are converted, during a scan, by each of said analog-to-digital converters, and for controlling entry of signals at said outputs of said analog-to-digital converters into said memory so that the signals from said detector elements are stored in said memory in a sequence corresponding to the order in which those detector elements were irradiated by said radiation.

* * * * *